United States Patent
Ohmori et al.

(10) Patent No.: US 6,388,098 B1
(45) Date of Patent: *May 14, 2002

(54) PROCESS FOR PREPARING ASCORBIC ACID-2-MONOPHOSPHATE SALT

(75) Inventors: Kazuhiro Ohmori, Chiba; Yuji Kobayashi; Tomokazu Soda, both of Kanagawa, all of (JP)

(73) Assignee: Showa Denko Kabushiki Kaisha, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/527,679

(22) Filed: Mar. 17, 2000

Related U.S. Application Data

(60) Provisional application No. 60/149,900, filed on Aug. 23, 1999.

(30) Foreign Application Priority Data

Mar. 18, 1999 (JP) ............................................. 11-074218

(51) Int. Cl.[7] ............................. C07F 9/06; C07F 9/08; C07D 307/62

(52) U.S. Cl. ........................ 549/222; 549/315; 549/316

(58) Field of Search ................................ 549/222, 315, 549/316

(56) References Cited

U.S. PATENT DOCUMENTS

| 3,658,848 A | | 4/1972 | Nomura et al. | |
|---|---|---|---|---|
| 4,179,445 A | | 12/1979 | Sieb et al. | |
| 5,149,829 A | * | 9/1992 | Seib et al. | 549/222 |
| 5,916,915 A | * | 6/1999 | Hong et al. | 514/474 |
| 6,063,937 A | | 5/2000 | Dlubala et al. | 549/218 |
| 6,124,274 A | * | 9/2000 | Schehlmann et al. | 514/99 |

OTHER PUBLICATIONS

Chemical Abstracts XP002186211, vol. 122, No. 19, May 8, 1995.

* cited by examiner

*Primary Examiner*—Ba K. Trinh
(74) *Attorney, Agent, or Firm*—Sughrue Mion, PLLC

(57) ABSTRACT

A process for preparing a high-purity ascorbic acid-2-monophosphate salt in a convenient manner and in a high yield, comprising hydrolyzing an ascorbic acid-2-polyphosphate or a salt thereof in the presence of magnesium ion at a pH of 7 or more.

12 Claims, No Drawings

PROCESS FOR PREPARING ASCORBIC ACID-2-MONOPHOSPHATE SALT

CROSS REFERENCE TO RELATED APPLICATIONS

This application is an application filed under 35 U.S.C. §111(a) claiming benefit pursuant to 35 U.S.C. S 119(e)(i) of the filing date of Provisional Application 60/149,900 filed Aug. 23, 1999 pursuant to 35 U.S.C. §111(b).

FIELD OF THE INVENTION

The present invention relates to a process for preparing conveniently an ascorbic acid-2-monophosphate salt, particularly an L-ascorbic acid-2-monophosphate (hereinafter sometimes abbreviated to "AsMP") salt in a high yield, by hydrolyzing an ascorbic acid-2-polyphosphate or a salt thereof, particularly an L-ascorbic acid-2-polyphosphate (hereinafter sometimes abbreviated to "AsPP") or a salt thereof, as the starting material in the presence of magnesium ion.

BACKGROUND OF THE INVENTION

L-Ascorbic acid (vitamin C) is known to have various physiological and pharmacological actions, and particularly by virtue of its effect of preventing melamine pigmentation, L-ascorbic acid has been used in whitening cosmetics. However, L-ascorbic acid is unstable to oxygen or heat, therefore, L-ascorbic acid derivatives stable against oxygen or heat have been heretofore formed by converting the hydroxyl group at the 2-position into a phosphate.

A salt, particularly a magnesium salt of L-ascorbic acid-2-monophosphate (hereinafter the "magnesium L-ascorbic acid-2-monophosphate" is sometimes abbreviated to "APM") is being used as a stabilized vitamin C derivative. APM exhibits excellent stability in cosmetic materials and scarcely decomposes. Furthermore, APM is easily absorbed through the skin and by the action of phosphatase present inside the human body, L-ascorbic acid is liberated to bring about various physiological actions such as prevention of melamine pigmentation.

High-purity AsMP salts are useful as a stabilized derivative of L-ascorbic acid and can be used in cosmetics, medical products, food additives, feed and other various industrial fields.

For monophosphorylating L-ascorbic acid, three methods described below are known. A first method comprises monophosphorylating L-ascorbic acid using phosphorus oxychloride as the phosphorylating agent and this method is described, for example, in JP-B-45-30328 (the term "JP-B" as used herein means an "examined Japanese patent publication"), JP-B-52-18191, JP-B-59-4438 and JP-A-2-27969 (the term "JP-A" as used herein means an "unexamined published Japanese patent application") and the like. The second method comprises transposing the phosphoric acid group of a phosphoric acid donor (e.g., adenosine triphosphate, pyrophosphoric acid and the like) to L-ascorbic acid using an enzyme and this method is described, for example, in JP-A-2-283283. The third method comprises reacting a soluble salt of metaphosphoric acid used as a phosphorylating agent with L-ascorbic acid and drying the aqueous solution to obtain AsMP salt and this method is described, for example, in JP-A-5-155893.

The first method above is most frequently used and according to Carbohydrate. Res., 67, 127–138 (1978), L-ascorbic acid-2-monophosphate is obtained as a main product in the form of tricyclohexylamine salt in a yield of 86%. The by-products are L-ascorbic acid-3-monophosphate, L-ascorbic acid-2-diphosphate (hereinafter sometimes abbreviated to "AsDP") and 2,2'-bis(L-ascorbic acid)phosphate. For the purification thereof, a complicated step such as ion exchange chromatography is necessary. L-ascorbic acid has four hydroxyl groups active in the reaction with phosphorus oxychloride and phosphorus oxychloride has three active sites, therefore, many by-products are produced. Furthermore, chloride ion generated from phosphorus oxychloride after the reaction is 3 molar times the phosphorus oxychloride used and this requires purification by electrodialysis and the like.

The second method is advantageous from the viewpoint that generation of by-products is prevented but still has the defect that the productivity is low. According to JP-A-2-283283, AsMP is produced using an enzyme fixed to an ion exchange resin and using diphosphoric acid (pyrophosphoric acid) as a phosphoric acid donor. However, the yield of AsMP of 34% is very low. Also, the amount of AsMP produced is as low as 1.7% in terms of the concentration in the reaction solution and large scale reaction equipment is necessary. Furthermore, in order to obtain high-purity AsMP salt, purification through many steps such as removal of a large amount of water and recovery of unreacted L-ascorbic acid is required.

The third method is a method of drying L-ascorbic acid-2-triphosphate (hereinafter sometimes abbreviated to "AsTP") in an aqueous solution and thereby stepwise hydrolyzing the phosphate bonded to produce AsMP. According to JP-A-5-155893, AsMP is produced by preparing an aqueous solution of AsTP from a soluble salt of metaphosphoric acid and L-ascorbic acid, adjusting the pH thereof to about 5.5 to 6.5 and performing drying at a temperature of from 120 to 180° C. As known from the pH of aqueous solution, this stepwise hydrolysis reaction of phosphate is acid hydrolysis reaction. Therefore, although it is set forth therein that sodium and calcium are advantageous as the cation present in the aqueous solution, the alkali property of the cation has no relation to the acid hydrolysis, since the pH of the aqueous solution is acidic.

Furthermore, the product AsMP obtained by this production method has extremely low purity and the yield is also low. As seen from the composition of the product obtained by this method described in the Examples, the AsMP purity is 61% and the yield based on AsTP is 66%. In addition, much L-ascorbic acid, AsDP and AsTP are present as by-products. The presence of L-ascorbic acid shows that the acid hydrolysis reaction of AsTP extended to L-ascorbic acid over AsMP.

This means that it is useless to phosphorylate the hydroxyl group at the 2-position of L-ascorbic acid so as to improve lack of stability of L-ascorbic acid to oxygen or heat. Furthermore, the L-ascorbic acid present in the product decomposes due to oxygen or heat causing coloration or produce oxalic acid which is a skin irritant. The product cannot be used in cosmetics and the like as it is. Therefore, the impurities must be purified by a complicated method such as ion exchange chromatography. For these reasons, this production method of AsMP by the drying of AsTP aqueous solution is not an industrial attractive.

As described above, AsMP salt is useful as a stabilized derivative of L-ascorbic acid, nevertheless, the production methods thereof are complicated and disadvantageous in industry. Under these circumstances, a simplified preparation process is demanded therefor.

SUMMARY OF THE INVENTION

As a result of extensive studies to eliminate the above-described defects, the present inventors have found that high-purity AsMP salt can be conveniently prepared in a high yield by hydrolyzing, preferably under heating AsPP, or a salt thereof at a pH of 7 or more as a starting material in the presence of magnesium ion. The present invention has been accomplished based on this finding of a new process.

The present invention provides the following embodiments for preparing an ascorbic acid-2-monophosphate salt:

(1) a process for preparing an ascorbic acid-2-monophosphate salt, comprising hydrolyzing an ascorbic acid-2-polyphosphate or a salt thereof in the presence of magnesium ion at a pH of 7 or more;

(2) the process as described in (1) above, comprising hydrolyzing a reaction product of an ascorbic acid and a polyphosphoric acid or a salt thereof in the presence of magnesium ion at a pH of 7 or more;

(3) the process as described in (1) above, comprising eating a mixture comprising:
  (A) an ascorbic acid-2-polyphosphate or a salt thereof,
  (B) water,
  (C) a magnesium compound capable of supplying magnesium ion in water, and
  (D) a base necessary for maintaining a pH of 7 or more;

(4) the process as described in (3) above, wherein the ascorbic acid-2-polyphosphate or a salt thereof (A) is one or more selected from the group consisting of an L-ascorbic acid-2-triphosphate and a salt thereof, an L-ascorbic acid-2-diphosphate and a salt thereof, and a mixture thereof;

(5) the process as described in (3) above, wherein the magnesium compound (C) is one or more selected from the group consisting of magnesium chloride, magnesium sulfate, magnesium acetate, magnesium nitrate, magnesium oxide, magnesium hydroxide, magnesium carbonate and a mixture thereof;

(6) the process as described in (3) above, wherein the base (D) is one or more selected from the group consisting of an alkali metal hydroxide, an alkali metal carbonate, an alkaline earth metal hydroxide, an alkaline earth metal oxide, an alkaline earth metal carbonate, a tertiary amine and a mixture thereof;

(7) the process as described in (3) above, wherein the compound serving both as the magnesium component (C) and the base (D) is one or more selected from the group consisting of magnesium hydroxide, magnesium oxide and magnesium carbonate;

(8) the process as described in (3) above, wherein the heating temperature is from 35° C. to the boiling point of the aqueous reaction solution;

(9) the process as described in (3) above, which includes, after the completion of reaction, adjusting the pH by adding an acid to the reaction solution or the diluted or concentrated solution to precipitate a phosphate salt and removing the phosphate salt;

(10) the process as described in (3) above, which includes, after the completion of reaction, adjusting the pH by adding an acid to the reaction solution or the diluted or concentrated solution to precipitate a phosphate salt and dissolving the precipitated phosphate salt and adding a base to the dissolved solution to precipitate the phosphate salt and removing the phosphate salt;

(11) the process as described in (9) above, which includes crystallizing an ascorbic acid-2-monophosphate salt from the aqueous reaction solution or an aqueous solution after the removal of phosphate using a water-soluble organic solvent; and

(12) the process as described in (11) above, which includes drying the wet ascorbic acid-2-monophosphate salt crystallized from the aqueous reaction solution or an aqueous solution after the removal of phosphate using a water-soluble organic solvent to obtain the ascorbic acid-2-monophosphate salt as a powder.

In the present invention, the ascorbic acid structure may be any of an L-form, a D-form and a racemic compound, however, the present invention is described below by referring to the L-form which is industrially useful.

According to the process of the present invention, an aqueous solution containing AsPP or a salt thereof is hydrolyzed, preferably under heating, at a pH of 7 or more in the presence of magnesium ion and thereby the phosphoric acid ester bond of AsPP is stepwise alkali-hydrolyzed to prepare AsMP.

This preparation process of the present invention comprises allowing magnesium ion to be present together and adjusting the pH to 7 or more, the stepwise hydrolysis from AsPP to AsMP proceeds almost constantly in quantity and the hydrolysis reaction from AsMP to L-ascorbic acid scarcely proceeds.

DESCRIPTION OF THE PREFERRED EMBODIMENTS

In the preparation process of the present invention, the ion allowed to be present at the hydrolysis cannot be just any alkaline earth metal ion but must be magnesium ion. The magnesium ion has an action of accelerating the hydrolysis reaction from AsPP to AsMP but not accelerating the hydrolysis from AsMP to L-ascorbic acid. The reasons therefor are not clearly understood but the magnesium ion maintains relatively mild alkalinity even in a strong alkali condition and has low water-solubility and these properties are considered to take a part in the above-described action.

For example, when magnesium oxide was added in 1.7 molar times to an aqueous solution containing AsMP and the solution was heated at 60° C. for 6 hours, the amount of residual AsMP was 100 wt %. When the same operation was performed using calcium oxide in place of magnesium oxide, the amount of residual AsMP was 41 wt % and this clearly showed formation of L-ascorbic acid and furthermore formation of oxalic acid by the decomposition of L-ascorbic acid. In the examination where magnesium chloride was added in 1.7 molar times to a solution containing AsMP sodium salt and heated at 60° C. for 6 hours, the amount of residual AsMP was also 100 wt %. However, when the same operation was performed using calcium chloride in place of magnesium chloride, the amount of residual AsMP was 63 wt %. The same results were obtained in the examination using barium ion in place of calcium ion.

As such, magnesium ion has an action of not accelerating the hydrolysis of AsMP but calcium ion and the like have no such an action. which can be used in the present invention include polyphosphoric acids such as triphosphoric acid, diphosphoric acid (pyrophosphoric acid) and metaphosphoric acid, and salts thereof. Accordingly, the AsPP usually includes AsTP, AsDP, and salts and mixtures thereof. These may be prepared by the method described in U.S. Pat. 5,149,829 and the like. In the present invention, the dehydration product of an ascorbic acid and a polyphosphoric acid or a salt thereof may be used as it is in the hydrolysis.

According to U.S. Pat. 5,149,829, an L-ascorbic acid and a polyphosphate salt such as sodium trimetaphosphate were reacted at a temperature of from 33 to 35° C. while adjusting the pH to 10.5 to 10.7 by NaOH or KOH. After the completion of reaction, the inorganic phosphoric acid compound was removed by precipitation as a calcium salt using calcium chloride at a temperature as low as 10° C. Thereafter, the residue was concentrated, crystallized from ethanol and dried to obtain the objective AsPP salt as a mixture of AsMP salt, AsDP salt and AsTP salt. In the method of U.S. Pat. 5,149,829, the inorganic phosphoric acid compound precipitated is removed, however, in the present invention, inorganic phosphoric acids may be mixed in the AsPP salt. In the case where use of AsPP as an acid but not as a salt is intended, the acid may be obtained by dissolving an AsPP salt in water and decationizing it by passing the solution through a strongly acidic cation exchange resin at a low temperature. Also, when use of only pure AsTP or only pure AsDP as a raw material is intended, the raw material may be obtained by purifying the AsPP using chromatography.

In the present invention, the AsPP concentration is, for example, in water, suitably from about 1 to 80 wt %. If the AsPP concentration is low, the reaction slowly proceeds, whereas it is excessively high, the viscosity increases or magnesium salt of AsPP precipitates. Accordingly, the AsPP concentration is preferably from about 5 to 50 wt %, more preferably from about 10 to 30 wt %.

Thereafter, magnesium ion is added to the aqueous solution of AsPP or a salt thereof. In the case where the AsPP is a salt, a water-soluble magnesium compound such as magnesium chloride is preferably used and in the case where the AsPP is an acid, a magnesium compound showing alkalinity such as magnesium oxide is preferably used. Examples of the magnesium ion-supplying compounds include magnesium chloride, magnesium sulfate, magnesium acetate, magnesium nitrate, magnesium oxide, magnesium hydroxide, magnesium carbonate and the like. These compounds may be used individually or as a mixture without any problem.

The amount of magnesium ion added is an equimolar amount or more to the phosphoric acid group of AsPP. As the alkali hydrolysis of AsPP proceeds, phosphoric acid is produced in the aqueous reaction solution and the phosphoric acid produced reacts with magnesium ion present in the aqueous reaction solution to form magnesium hydrogenphosphate or magnesium phosphate. These magnesium salts of phosphoric acid have very low solubility in water and accordingly precipitate out. As a result, magnesium ion in the aqueous solution necessary for the hydrolysis reaction decreases. Accordingly, in order to maintain the magnesium ion in the reaction system even when the hydrolysis reaction of AsPP proceeds, the magnesium ion is required in an equimolar amount or more to the phosphoric acid group of AsPP. In this reaction, the amount of magnesium ion added has no upper limit in particular, however, the presence of excess magnesium ion has no effect on the reaction and this is of no benefit. Accordingly, the amount of magnesium added is preferably from about 1.1 to 2.0 mol, more preferably from 1.3 to 1.8 mol, based on the phosphoric acid group of AsPP.

In the preparation process of the present invention, the pH is suitably set to be 7 or more. If the pH is less than 7, the stepwise hydrolysis reaction in the present invention becomes hydrolysis accelerated by an acid, as a result, the hydrolysis of the objective product AsMP is also accelerated to decompose it into L-ascorbic acid and phosphoric acid. Accordingly, the aqueous reaction solution must be set to a pH of 7 or more using an appropriate alkali. Examples of the alkali used here include alkali metal hydroxides, alkali metal carbonates, alkaline earth metal hydroxides, alkaline earth metal oxides, alkaline earth metal carbonates, tertiary amines, and mixtures of two or more thereof. In the case where the alkaline earth metal compound used is magnesium oxide, magnesium hydroxide or magnesium carbonate, magnesium ion can be supplied to the aqueous reaction solution and thus actions of adjusting the pH and at the same time accelerating the hydrolysis of AsPP can be achieved. In the present invention, substantially no problem arises as long as the pH is 7 or more. However, the reaction slowly proceeds in the alkali region closer to the neutral, whereas reaction in the strong alkali condition requires alkali-resistant equipment. Accordingly, the pH is preferably from 8 to 13, more preferably from 9 to 11.

In addition, heating is preferably performed in the present invention. If the reaction is performed at a low temperature, a very long time is necessary until the completion of reaction and the plant is not utilized efficiently and this is disadvantageous. Accordingly, the reaction is preferably performed at a temperature of from 35° C. to the boiling point of aqueous reaction solution, more preferably from 50 to 90° C.

The thus-obtained AsMP-containing aqueous solution is diluted or concentrated to an appropriate AsMP concentration and a phosphate salt precipitated (example: phosphoric acid alkali salt) is removed by the solid-liquid separation. At this time, the pH is adjusted with an appropriate acid to effectively precipitate the phosphate salt. Examples of said acid are concentrated or diluted hydrochloric acid. Or, the phosphate salt precipitated may be dissolved by an acid and again precipitated by adding a base.

In the aqueous solution containing high-purity AsMP salt after the removal of the phosphate salt precipitated, AsMP salt is precipitated using a water-soluble organic solvent. Examples of the water soluble organic solvent used here include methanol, ethanol, isopropanol, tetrahydrofuran, dioxane, acetone and the like. Among these, ethanol is preferred in view of the cost and ease of recovery.

The thus-obtained wet AsMP salt is dried by vacuum drying or fluidized bed drying to obtain AsMP salt in a high yield.

In particular, AsMP magnesium salt has excellent stability against heat or light, accordingly, it is used not only for cosmetic powders or lotions but also, for example, for medical products (e.g., oral cavity preparation, eyedrops, products for bath and the like), cosmetics (e.g., lotion, emulsion, cream, pack and the like), food (e.g., bread and the like) and animal feed (e.g., feed for breeding prawn, salmon, yellow tail, eel, carp and the like).

EXAMPLES

The present invention is described in greater detail below by referring to Examples, however, the present invention should not be construed as being limited thereto. In Examples, "%" is "% by weight (wt %)".

Example 1

300 g (1.7 mol) of L-ascorbic acid was dissolved in 1,050 ml of ion exchanged water and the resulting solution was adjusted to a pH of 11 with 48% NaOH. To this solution, 710 g (2.3 mol) of sodium trimetaphosphate was added and reacted for 24 hours while keeping the temperature at from 30 to 35° C. During the reaction, the adjustment of pH with 48% NaOH was continued so as to keep the pH of the aqueous reaction solution at from 10.5 to 10.7. After the completion of reaction, 1,750 ml of ion exchanged water was added and the resulting solution was cooled to 10° C. To this aqueous solution, 100 ml of a 2.5 M aqueous calcium chloride solution was added and then pH was adjusted to about 7 to precipitate inorganic phosphates salts. The filtrate was concentrated to further remove inorganic phosphate salts by precipitation and thereafter, AsPP salt was precipitated using ethanol and centrifuged to obtain wet AsPP salt. The wet salt obtained was washed with 50% ethanol and then vacuum dried to obtain the starting material AsPP salt of this Example as a mixture of AsMP salt, AsDP salt and AsTP salt (yield: 87%).

Thereafter, 300 g of AsPP salt was dissolved in 1,500 ml of ion exchanged water and the resulting solution was passed through a strongly acidic cation exchange resin and converted into AsPP. This aqueous solution was diluted with ion exchanged water to have an AsPP concentration of 10%.

To 1,000 ml of an aqueous solution containing 10% of AsPP (AsMP:AsDP:AsTP =0.035 mol: 0.052 mol: 0.175 mol), 48 g (1.2 mol) of magnesium oxide was added with stirring at room temperature in a nitrogen atmosphere. Then, the resulting solution was adjusted to a pH of 9.5 with 48% NaOH and continuously heated for 4 hours while keeping the solution at a temperature of from 75 to 80° C. and while appropriately adjusting the pH with 48% NaOH so as to always keep the pH at 9.5 or more during the reaction. After the completion of reaction, the product was analyzed by HPLC (high-performance liquid chromatography), as a result, it was found that the amount of AsMP produced was 0.26 mol, AsDP was present in a trace amount and AsTP was completely absent. This reaction solution was cooled to room temperature (about 20–30° C.) and the precipitate was removed by a centrifugal separator.

To about 950 ml of the thus-obtained AsMP salt-containing solution, 1,900 ml of 95% methanol was added dropwise over 4 hours. After the completion of dropwise addition, stirring was further continued for 1 hour to ripen the solution, and wet AsMP salt precipitated was collected by filtration and thoroughly washed with 300 ml of 95% methanol.

The resulting wet salt was dried at 40° C. in vacuum, then, 94.5 g (yield 93%) of AsMP magnesium salt (APM.5H$_2$O) having a purity of 98% was obtained.

Example 2

The starting material AsPP salt was prepared in the same manner as in Example 1.

Thereafter, 300 g of AsPP salt was dissolved in 1,500 ml of ion exchanged water and the resulting solution was passed through a strongly acidic cation exchange resin and converted into AsPP. This aqueous solution was diluted with ion exchanged water to have an AsPP concentration of 10%.

To 1,000 ml of an aqueous solution containing 10% of AsPP (AsMP:AsDP:AsTP =0.035 mol: 0.052 mol: 0.175 mol), 83 g (0.86 mol) of magnesium carbonate was added while stirring at room temperature in a nitrogen atmosphere. Then, the resulting solution was adjusted to a pH of 10.5 with 40% KOH and continuously heated for 8 hours while keeping the solution at a temperature of from 55 to 60° C. and while appropriately adjusting the pH with 48% KOH so as to always keep the pH at 10.5 or more during the reaction. The reaction solution was allowed to cool to room temperature and then the precipitate was dissolved by adjusting the pH to about 3 with 35% hydrochloric acid. To the solution, magnesium oxide was added until the pH reached 10 and then the precipitate was removed by a centrifugal separator.

To about 1,000 ml of the thus-obtained AsMP salt-containing solution, 2,000 ml of 95% methanol was added dropwise over 4 hours. After the completion of dropwise addition, stirring was further continued for 1 hour to ripen the solution, and wet AsMP salt precipitated was collected by filtration and thoroughly washed with 300 ml of 95% methanol.

The resulting wet salt was dried at 40° C. in vacuum, then, 92.4 g (yield 91%) of AsMP magnesium salt (APM.5H$_2$O) having a purity of 98% was obtained.

Example 3

The starting material AsPP salt was prepared in the same manner as in Example 1.

Thereafter, 300 g of AsPP salt was dissolved in 750 ml of ion exchanged water and the resulting solution was passed through a strongly acidic cation exchange resin and converted into AsPP. This aqueous solution was adjusted to a pH of 8.5 by adding thereto 48% NaOH to prepare AsPP sodium salt. Furthermore, the solution was diluted with ion exchanged water to have an AsPP concentration of 20%.

To 1,000 ml of an aqueous solution containing AsPP sodium salt (AsMP:AsDP:AsTP =0.070 mol: 0.104 mol: 0.35 mol) and having an AsPP content of 20%, 227 g (2.4 mol) of magnesium chloride was added while stirring at room temperature in a nitrogen atmosphere. Then, the resulting solution was adjusted to a pH of 8.5 with 48% NaOH and continuously heated for 10 hours while keeping the solution at a temperature of from 65 to 70° C. and while appropriately adjusting the pH with 48% NaOH so as to always keep the pH at 8.5 or more during the reaction. The reaction solution was allowed to cool to room temperature, the pH was adjusted to 10 with 48% NaOH, and the precipitate was removed by a centrifugal separator.

The residue was crystallized in the same manner as in Example 1, then AsMP salt was obtained in a yield of 85%.

Example 4

The starting material AsPP salt was prepared in the same manner as in Example 1.

Thereafter, 600 g of AsPP salt was dissolved in 1,500 ml of ion exchanged water and the resulting solution was passed through a strongly acidic cation exchange resin and converted into AsPP. This aqueous solution was adjusted to a pH of 7.5 by adding thereto 40% KOH to prepare AsPP potassium salt. Furthermore, the solution was concentrated using an evaporator to have an AsPP concentration of 30%.

To 1,000 ml of an aqueous solution containing AsPP potassium salt (AsMP:AsDP:AsTP =0.105 mol: 0.156 mol: 0.525 mol) and having an AsPP content of 30%, 308 g (2.6 mol) of magnesium sulfate was added while stirring at room temperature in a nitrogen atmosphere. Then, the resulting solution was adjusted to a pH of 7.5 with 40% KOH and continuously heated for 16 hours while keeping the solution at a temperature of from 45 to 50° C. and while appropriately adjusting the pH with 40% KOH so as to always keep the pH at 7.5 or more during the reaction. The reaction solution was allowed to cool to room temperature, 1,000 ml of ion exchanged water was added thereto, the pH was adjusted to 10 with 40% KOH, and the precipitate was removed by a centrifugal separator.

The residue was crystallized in the same manner as in Example 1, then, AsMP salt was obtained in a yield of 81%.

Comparative Example 1

The starting material AsPP salt was prepared in the same manner as in Example 1, and thereafter, AsPP was prepared using an ion exchange resin.

The reaction was performed under the same conditions as in Example 1 except for using calcium oxide in place of magnesium oxide. After the completion of reaction, the reaction solution was allowed to cool to room temperature and the precipitate was removed by a centrifugal separator.

The thus-obtained AsMP salt-containing solution was crystallized with methanol and dried, then, AsMP salt having a purity of 74% was obtained in a yield of 41%. In this AsMP salt, a large amount of oxalic acid was mixed.

According to the preparation process of the present invention, an ascorbic acid-2-monophosphate salt having a high purity and reduced in coloration can be prepared in a convenient manner and in a high yield.

The ascorbic acid-2-phosphate salts such as magnesium L-ascorbic acid-2-monophosphate obtained by the preparation process of the present invention, may be used in cosmetics, feed, medical products, food additives and the like.

While the invention has been described in detail and with reference to specific embodiments thereof, it will be apparent to one skilled in the art that various changes and modifications can be made therein without departing from the spirit and scope thereof.

What is claimed is:

1. A process for preparing an ascorbic acid-2-monophosphate salt, comprising hydrolyzing an ascorbic acid-2-polyphosphate or a salt thereof in the presence of magnesium ion at a pH of 7 or more.

2. The process as claimed in claim 1, comprising hydrolyzing a reaction product of an ascorbic acid and a polyphosphoric acid or a salt thereof in the presence of magnesium ion at a pH of 7 or more.

3. The process as claimed in claim 1, comprising hydrolyzing by heating a mixture comprising:

(A) an ascorbic acid-2-polyphosphate or a salt thereof;
    (B) water;
    (C) a magnesium compound capable of supplying magnesium ion in water; and
    (D) a base necessary for maintaining a pH of 7 or more.

4. The process as claimed in claim 3, wherein the ascorbic acid-2-polyphosphate or a salt thereof (A) is one or more selected from the group consisting of an L-ascorbic acid-2-triphosphate and a salt thereof, an L-ascorbic acid-2-diphosphate and a salt thereof, and a mixture thereof.

5. The process as claimed in claim 3, wherein the magnesium compound (C) is one or more selected from the group consisting of magnesium chloride, magnesium sulfate, magnesium acetate, magnesium nitrate, magnesium oxide, magnesium hydroxide, magnesium carbonate and a mixture thereof.

6. The process as claimed in claim 3, wherein the base (D) is one or more selected from the group consisting of an alkali metal hydroxide, an alkali metal carbonate, an alkaline earth metal hydroxide, an alkaline earth metal oxide, an alkaline earth metal carbonate, a tertiary amine and a mixture thereof.

7. The process as claimed in claim 3, wherein the compound serving both as the magnesium component (C) and the base (D) is one or more selected from the group consisting of magnesium hydroxide, magnesium oxide and magnesium carbonate.

8. The process as claimed in claim 3, wherein the heating temperature is from 35° C. to the boiling point of the aqueous reaction solution.

9. The process as claimed in claim 3, which includes, after the completion of reaction, adjusting the pH by adding an acid to the reaction solution or the diluted or concentrated solution to precipitate a phosphate salt and removing the phosphate salt.

10. The process as claimed in claim 3, which includes, after the completion of reaction, adjusting the pH by adding an acid to the reaction solution or the diluted or concentrated solution to precipitate a phosphate salt and dissolving the precipitated phosphate salt and adding a base to the dissolved solution to precipitate the phosphate salt and removing the phosphate salt.

11. The process as claimed in claim 9, which includes crystallizing an ascorbic acid-2-monophosphate salt from the aqueous reaction solution or an aqueous solution after the removal of phosphate using a water-soluble organic solvent.

12. The process as claimed in claim 11, which includes drying the wet ascorbic acid-2-monophosphate salt crystallized from the aqueous reaction solution or an aqueous solution after the removal of phosphate using a water-soluble organic solvent to obtain the ascorbic acid-2-monophosphate salt as a powder.

* * * * *